(12) United States Patent
Wolfe et al.

(10) Patent No.: US 10,806,358 B2
(45) Date of Patent: Oct. 20, 2020

(54) INTEGRATED THIN-FILM OPTRODE

(71) Applicants: University of Houston System, Houston, TX (US); Vanderbilt University, Nashville, TN (US)

(72) Inventors: John C. Wolfe, Houston, TX (US); Mufaddal Gheewala, Hillsboro, OR (US); Wei-Chuan Shih, Houston, TX (US); Gopathy Purushothaman, Pondicherry (IN)

(73) Assignees: UNIVERSITY OF HOUSTON SYSTEM, Houston, TX (US); VANDERBILT UNIVERSITY, Nashville, TN (US)

( * ) Notice: Subject to any disclaimer, the term of this patent is extended or adjusted under 35 U.S.C. 154(b) by 276 days.

(21) Appl. No.: 15/973,077

(22) Filed: May 7, 2018

(65) Prior Publication Data

US 2018/0325379 A1 Nov. 15, 2018

Related U.S. Application Data

(62) Division of application No. 14/287,760, filed on May 27, 2014, now Pat. No. 9,986,914.

(Continued)

(51) Int. Cl.
*A61B 5/04* (2006.01)
*A61B 5/0478* (2006.01)
(Continued)

(52) U.S. Cl.
CPC ........ *A61B 5/04001* (2013.01); *A61B 5/0084* (2013.01); *A61B 5/0478* (2013.01);
(Continued)

(58) Field of Classification Search
CPC .......................... A61B 5/04001; A61B 5/0478
See application file for complete search history.

(56) References Cited

U.S. PATENT DOCUMENTS

| 5,525,542 A | 6/1996 | Maniar |
| 5,917,330 A * | 6/1999 | Miley ................ G01R 1/07342 |
| | | 324/754.07 |

(Continued)

FOREIGN PATENT DOCUMENTS

WO 2004038430 A2 5/2004

*Primary Examiner* — Lee S Cohen
(74) *Attorney, Agent, or Firm* — Winstead PC

(57) ABSTRACT

An optrode may provide a cylindrical substrate with two or more electrodes deposited on said cylindrical substrate. The cylindrical substrate and electrodes may be coated by an insulating layer with openings or vias over certain portions of the electrodes that may provide a contact for the neural probe or may be utilized to connect lead lines. Manufacturing of an optrode may utilize a jig that secures a cylindrical substrate coated by a conductive material and a resist. A first mask may be positioned in an opening provided by the jig, and the cylindrical substrate may expose ions or neutral particles to define one or more electrode patterns. After regions of the resist and conductive material are removed to form the electrodes, a second mask may be utilized to define via regions in which portions of the electrodes are exposed and uncoated by an insulating layer.

18 Claims, 7 Drawing Sheets

Related U.S. Application Data

(60) Provisional application No. 61/827,192, filed on May 24, 2013.

(51) Int. Cl.
*A61B 5/00* (2006.01)
*H01L 31/0224* (2006.01)
*H01L 33/38* (2010.01)

(52) U.S. Cl.
CPC .... *H01L 31/022408* (2013.01); *H01L 33/382* (2013.01); *A61B 5/4064* (2013.01); *A61B 2562/12* (2013.01)

(56) References Cited

U.S. PATENT DOCUMENTS

| | | | |
|---|---|---|---|
| 6,560,472 B2 | 5/2003 | Hill | |
| 7,010,356 B2 | 3/2006 | Mandar | |
| 7,190,989 B1 * | 3/2007 | Swanson | A61B 5/0478 600/378 |
| 7,504,619 B2 | 3/2009 | Wolfe | |
| 8,229,539 B1 * | 7/2012 | Motoyoshi | A61B 5/04001 600/378 |
| 8,661,663 B2 * | 3/2014 | Wolfe | A61B 5/0478 29/830 |
| 9,801,559 B2 * | 10/2017 | Jamieson | A61B 5/6848 |
| 2006/0017917 A1 | 1/2006 | Cullum | |
| 2006/0038990 A1 | 2/2006 | Habib | |
| 2008/0140195 A1 | 6/2008 | Su | |
| 2016/0143551 A1 * | 5/2016 | Yoon | A61B 5/04001 600/373 |

* cited by examiner

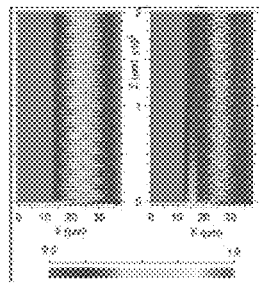 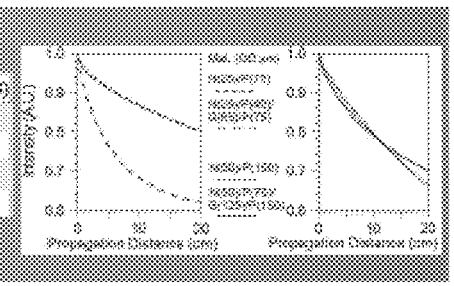
FIG. 9B    FIG. 9C                    FIG 9D
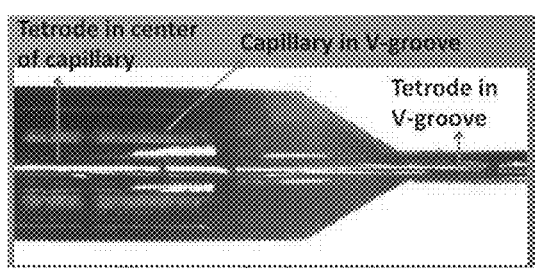 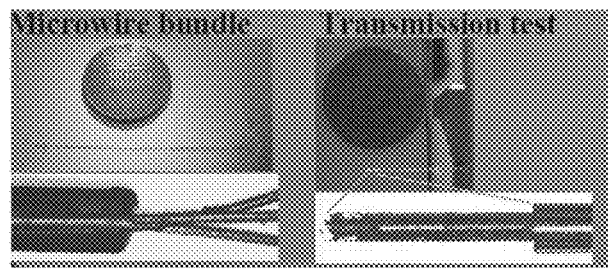
FIG. 9G    FIG. 9H    FIG. 9I
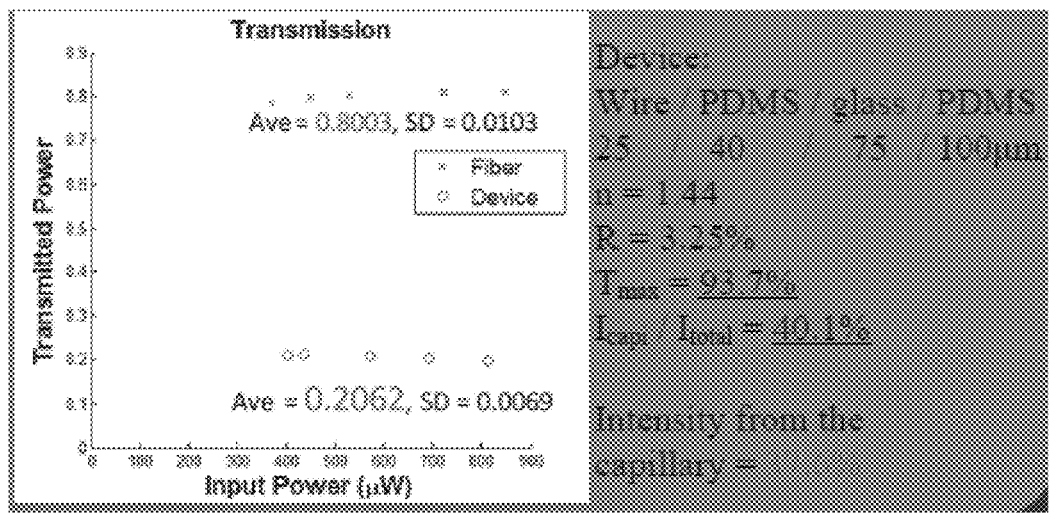
FIG. 9J

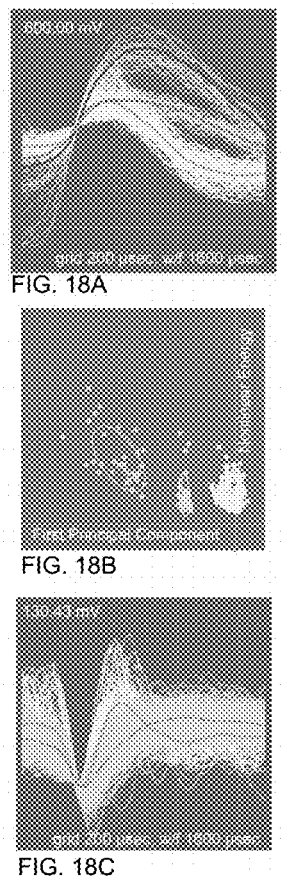
FIG. 18A
FIG. 18B
FIG. 18C
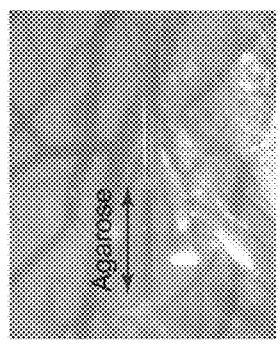
FIG. 17
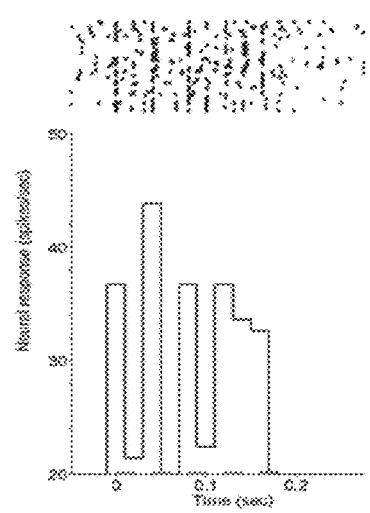
FIG. 19
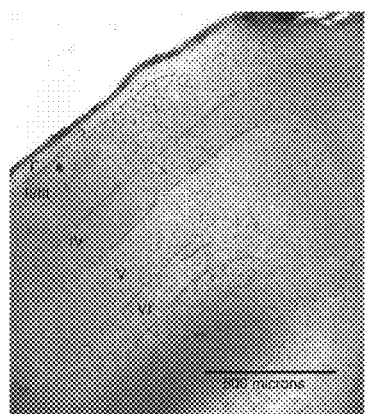
FIG. 20A
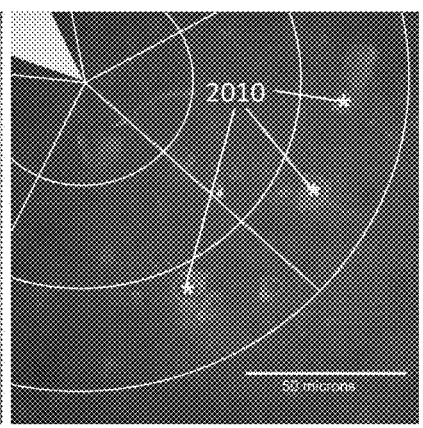
FIG. 20B

INTEGRATED THIN-FILM OPTRODE

RELATED APPLICATIONS

This application is a divisional application of U.S. Pat. No. 9,986,914 issued on Jun. 5, 2018, which claims the benefit of U.S. Provisional Patent Application No. 61/827,192, filed on May 24, 2013, which are incorporated herein by reference.

FIELD OF THE INVENTION

This invention relates to neural probes and methods of manufacturing neural probes, more particularly, the neural probes may be multi-tiered neural probes that can be utilized in a probe array.

BACKGROUND OF INVENTION

Optogenetic interrogation and isolation of photostimulated neurons: The function of a cortical neuron depends on its microcircuitry—the inputs it receives from local and long-range connections and the outputs it sends to other neurons. The existence of synaptic connections between two neurons can be inferred using neuroanatomical tracing but these methods cannot determine the frequency and strength of synaptic connections. Connectivity is often inferred during in vivo experiments by electrically or chemically stimulating a cluster of neurons and observing the effect on potential target neurons. However, both electrical and chemical stimulation indiscriminately activate a large group of neurons thus making it impossible to determine specific synaptic connections. In addition, cortical neurons receive inputs from the same source region via multiple pathways. Optogenetics can determine neural circuits with greater specificity and precision than previously possible. In particular, it has been recently demonstrated that viral vectors and in utero electroporation can be used to express light-sensitive channelrhodopsin-2 (ChR2) in a specific group of genetically determined neurons. Remarkably, when introduced in this manner, ChR2 is expressed not only near the cell bodies but is also transported to distant axon terminals. Injecting a viral vector carrying the gene for ChR2 into a cortical area resulted in the expression of ChR2 in axons within the thalamic projection zone of this cortical area. Photostimulation of these axons and the measurement of the photo-evoked activity then provide information about the direct influence exerted by this specific group of cortical neurons on their target neurons in this specific thalamic nucleus. Already, a handful of studies have used this technique to make exciting discoveries about specific brain areas that are involved in specific behaviors.

While great progress has been made in genetic methods used in optogenetics, little has been made in improving the devices used to simultaneously photostimulate and record neural activity (optrodes). These devices are made by either gluing microwires or electrodes to commercially available, thick optical fibers (e.g. ~400-500 microns). To realize the full potential of optogenetic methods, a new type of optrode is required. This optrode should be capable of reaching many areas of interest buried within cortical sulci, deep subcortical structures like the amygdala, basal ganglia and the thalamus, as well as the brain stem. It should be therefore thin enough not to displace too much tissue or do much damage during repeated penetrations but at the same time it should be rigid enough to hit the target areas stereotaxically. It should be capable of delivering a significant amount of light power (~100 mW) at its tip. Most important, it should provide electrodes with high signal-to-noise ratios and an optimized geometry for isolating single unit activity near the tip and in higher layers far from the region of direct photostimulation. The technology should include a simple method for interfacing the probes with standard neuroamplifier and signal processing systems and for fabricating linear and 2-D probe arrays. Finally, it should be compatible with automated manufacturing.

The design of a static probe with the 3-D mapping capability needed for the studies just described has been the subject of extensive theoretical and experimental investigation. Some have concluded that it will take 6 tiers of 4-channel sensors (tetrodes) on 10 μm pitch to acquire the rich data set needed to map the positions of neuronal dipoles with a precision equal to 10% of the recording volume. To access undisturbed tissue ahead of the probe and measure the activity of photostimulated neurons where the light field is most intense, each tetrode needs to be within about 60 micrometers of the tip. Thus, the setback of the first tetrode should be on the order of 10 μm. Moreover, the mapping of synchronous spike activity in ensemble studies may require electrode site diameters equal to or below about 5 μm. These specifications are far beyond the capability of current technology.

3-D mapping of neuronal dipoles: Modular organization is a hallmark of sensory cortex. Modules can be radial (e.g., orientation and ocular dominance columns, dendritic and pyramidal cell minicolumns) or tangential (e.g., cortical layers, cell rows). Driving inputs, feedback inputs, and outputs to a cortical neuron are largely determined by the layer in which the neuron is located. Neurons with similar functional properties are clustered into radial modules and arranged across the cortical surface in "functional maps." Across species and cortical areas, estimated sizes of functional modules are 50 μm for a single orientation column in area V1 and in motor cortex; 250 μm for a cytochrome oxidase (CO) patch and color blobs in area V2; and 500 μm for an ocular dominance column in V1. Estimated sizes of anatomical modules are 22 μm for pyramidal cell modules in mouse barrel cortex; 60 μm in rat V1; 30-80 μm for ontogenic columns in various species; and 400-500 μm for projection fields or afferent columns in many species. Thus, local connections and functional properties of neurons can change in a few tens of microns. During extracellular recording of single or multiunit action potentials, the precise location of recorded neurons is unknown. As a result, sampled neurons have diverse functional properties and connectivity. When these neurons are pooled together and a hypothesis is tested, inconsistent results can be obtained depending on the chance constitution of the sample, generating controversies. Even basic questions about the size, constitution, and physiological properties of cortical minicolumns have not been settled 60 years after their discovery. A major impediment is the poor spatial resolution of the extracellular recording method. With such uncertain localization, it would be impossible to show that a receptive field property differs systematically from one minicolumn to the next. Such inherent limitations have plagued efforts to show that the minicolumn (or the column for that matter) has distinct properties and borders.

Extracellular recording locations are marked with small electrical lesions of tissue which can be identified post mortem during histological analysis. Recent techniques for such ex vivo localization of electrode tips include improved electrical lesioning and fluorescent dye-coated electrodes. Lesions and fluorescent traces are typically 50-400 μm wide, yielding an accuracy of 25-200 µm. About 95% of recorded neurons are distributed over a 132 µm radius of the extracellular electrode. Therefore, even if the electrode tip were localized using a state-of-the-art method, there will still be an uncertainty of at least ~(50+132)=~182 µm in the actual spatial location of the spike source. This region of uncertainty can encompass several functional and anatomical minicolumns. Localization uncertainty can be reduced further by coupling a tip-locating method with a monopole or dipole source localization procedure as describe above, thereby reducing post mortem localization uncertainty to ~75 µm.

A few methods for in vivo localization of electrode tips have been developed, such as stereo x-ray imaging, coregistration of CT and MRI images, and of photograph-MRI-radiographs. However, localization errors of these methods are estimated to range ~150-1000 µm, too large for source localization methods to be useful. Clearly advances in real time tip localization would have a terrific impact since then the exact location of active neurons anywhere in the brain could be determined with ~50 µm accuracy or better.

The probe technology discussed herein may be used for source localization in conjunction with ex vivo techniques (see Validation section below). Finally, electrode tips are sometimes localized either in vivo or ex vivo with respect to an optically imaged functional map. However, prior art methods are in need of probes capable of localizing spike sources accurately.

Consider a specific example of how our probes can resolve major controversies. Across the surface of area V1, neurons are arranged as an orderly map of preferred orientation with occasional singularities. Optical imaging has showed that preferred orientation continuously changes around the singularity point, with iso-orientation domains converging to the point like the vanes of a pinwheel. The organization of pinwheel centers remains controversial. The magnitude of the optically imaged orientation signal at pinwheel centers is quite low. This could be due to either the pinwheel-center neurons being inherently poorly tuned for orientation or the orientation preference of pinwheel-center neurons changing abruptly in a very short distance, thereby smearing the optical signal. Single and multi-electrode array recordings, optical and 2-photon imaging, and other methods have yielded contradictory evidence. Some studies concluded that selectivity for orientation near pinwheels is sharp, others that it is broad, and yet others that there is no consistent relationship between pinwheel structures and orientation selectivity. This disagreement stems from the spatial localization error of current mapping methods. Typically, 6-8 orientation samples are used to estimate the preferred orientation of a neuron.

Based on the conservative estimate of 75 µm spatial resolution for our probes, we can deduce that neurons can be densely sampled and selectively assigned to 6-8 confidence bands, each 75 µm wide, around a pinwheel center. This should allow the precise mapping of orientation preference as close as ~70 µm from the exact pinwheel center (i.e., $[75*6/(2*\pi)]$). As this example illustrates, our probes will help advance systems neuroscience by enabling the mapping of structure-function relationship in the cortex with significantly improved precision.

Multi-tiered neural probes and methods for manufacturing such probes are discussed herein. Systems and methods discussed herein integrate thin film electrodes and associated interconnect wiring on the cylindrical surface of optical fibers and other cylindrical or multi-sided wire substrates. In some embodiments, the neural probe may be an optrode and/or a tetrode. The neural probes may enable users to optically stimulate the axonal arbors of a specific group of genetically determined neurons, however deep in the brain these arbors might be, and record spikes from activated neurons in the vicinity of the fiber tip as well as at higher levels along the probe shank. Furthermore, dense arrays of such fine optrodes will enable neuroscientists to independently manipulate neurons at multiple sites with high spatial and temporal resolution. These advances may allow systems neuroscientists to establish causal relationships between different groups of neurons and map brain circuits with unprecedented specificity and precision.

SUMMARY OF THE INVENTION

In one embodiment, a neural probe may provide a cylindrical substrate. The cylindrical substrate may have one or more tiers of conductive lines and electrodes on the surface of the cylindrical substrate. The cylindrical substrate and electrodes may be coated by a nonconductive material or insulator layer. One or more regions over the electrodes may remain uncoated by the nonconductive material layer to provide vias allowing access of cerebro-spinal fluid to the electrode sites and over conductive lines to allow for coupling to external devices, such as, but not limited to, a data recorder, signal processor, amplifier, or the like.

In another embodiment, manufacturing of a neural probe may utilize a jig that secures a cylindrical substrate coated by a conductive material and a resist. A first mask may be positioned in an opening provided by the jig that allows the cylindrical substrate to be exposed to ions or neutral particles utilized to define one or more conductor line(s) and electrode site(s). After regions of the resist and conductive material are removed to form the conductor lines and electrodes, the cylindrical substrate may be coated with a nonconductive material or insulator layer that covers the conductor lines and electrodes. A second mask may be utilized to define regions of the nonconductive material layer, which are removed to provide vias that expose portions of the conductor lines and electrode sites.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIGS. 9A-9J are illustrative embodiments of a capillary guided assembly and corresponding testing results;

FIG. 17 shows a surgical microscope photo of cortical penetration of the probe;

FIGS. 18A-18C show neural spikes measured in vivo by one channel of a 3-channel probe from cortical surface;

FIG. 19 shows a histogram of the in-vivo neural response to 5 laser pulses; and

FIGS. 20A-20B show a coronal section and high magnification fluorescence micrograph of a white boxed region.

DETAILED DESCRIPTION

Figure 1:
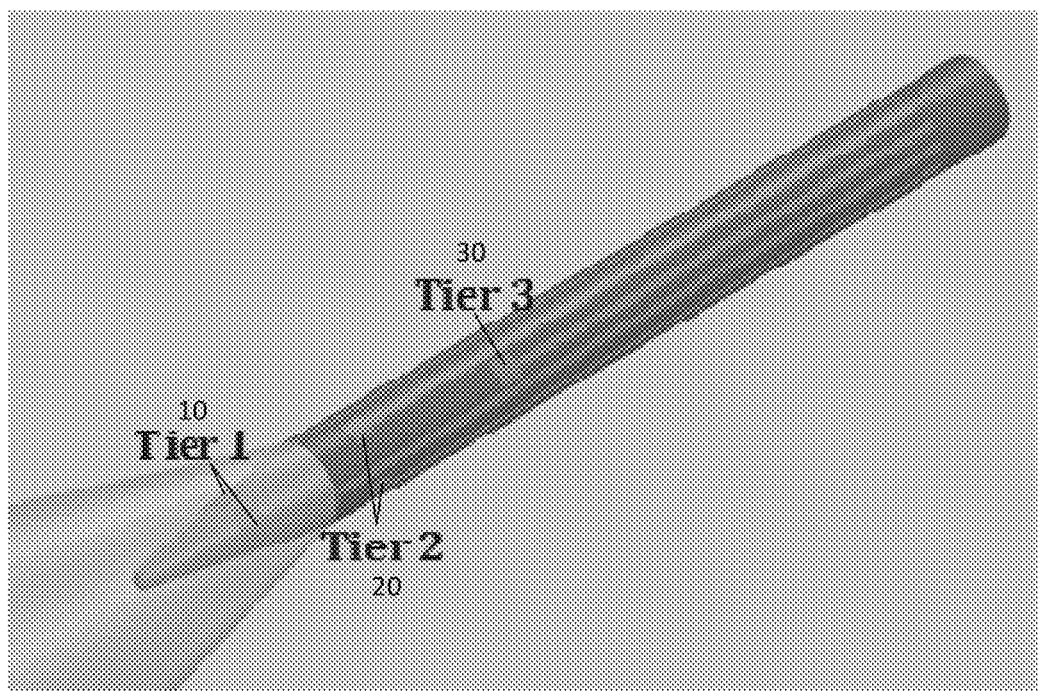
FIG. 1 is an illustrative embodiment of an integrated thin-film optrode with 3 tiers of 4-channel (tetrode) sensors on an optical fiber substrate.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The neural probes discussed herein will allow neuroscientists to record from a large number of neurons, and to precisely estimate the location and dipole strength of spiking neurons within the recording volume. Further, the probes may be utilized for optogenetics, such as to manipulate the activity of a chosen subset of these neurons in space and time. These probes significantly reduce the size and increase the density of electrode sites on deep brain probes relative to the state of the art, thus enabling 3-D mapping of spiking neurons with a resolution approaching 5% of the recording volume of state-of-the-art nonplanar tetrodes. These probes will give neuroscientists the power to investigate the structure and function of neural circuits where the local connections and functional properties of neurons, which can change in a few tens of microns. An example is cortical minicolumns where even basic questions about the size, constitution, and physiological properties have not been settled 60 years after their discovery. The probes can be implanted on cortical surface as well as in deep brain regions (e.g. cortical sulci, subcortical structures, and the brain stem), for which micromachined silicon probes are too short. The fabrication of such powerful probes is now feasible due to the development of a unique toolset discussed herein that enables the integration of thin film electrodes (e.g. micron scale or smaller) and associated interconnect wiring on the cylindrical surface of fine optical fibers with tight manufacturing tolerances (e.g. 0.25 µm). The probes may use optical fibers as probe substrates, which provide high intensity, multispectral light delivery with essentially no coupling loss, as well as the strength and stiffness required for deep-brain applications. The use of thin film conductors contributes negligibly to the probe diameter. In some embodiments, the probe diameter may be equal to or less than 60 µm. In some embodiments, the probe diameter may be equal to or less than 30 µm. Further, the high resolution and high dimensional precision of the fabrication process permits a very high electrode count on thin fibers and enables accurate 3-D localization of neuronal sources. Moreover, the technology is compatible with high throughput manufacturing at very low cost, an important consideration for wide dissemination of the technology, such as for linear and 2D-array applications. In some embodiments, the probe may include a zero-insertion-force connector to interface thin-film wiring on the (cylindrical) probe and commercial neuro-amplifier/signal processing systems.

Multiple electrodes may be provided by the neural probe, such as electrode sites and conductor lines running along the shank of the probe. The neural probe may provide multiple conductor lines arranged on a cylindrical or multifaceted substrate. The cylindrical substrate may be an optical fiber, needle, or wire. Neural probes may include multiple layers deposited on an optical fiber, such as, but not limited to, cladding and/or insulating layers. In some embodiments, the neural probes may include multiple conductor, cladding, and/or insulator layers. In some embodiments, the multiple conductor lines may form multiple sets, wherein each set constitutes a channel. In some embodiments, the probe may form a multi-channel probe. As a nonlimiting example, the multi-channel probe may be a tetrode, which is a neural probe that provides four sets of conductor lines and electrode sites or four channels. In some embodiments, each set of conductor lines may provide multiple tiers of electrode sites. The multi-tier probes provide electrode sites that are offset into different tiers along the central axis of the optical fiber, or in other words, the electrode contacts for each tier may be positioned at different distances from the tip of the probe. As a nonlimiting example, the neural probe may provide a six-tier, four-channel probe, which provides four sets of six conductor lines and electrode sites, wherein the six electrode sites in each set are offset into different tiers along the central axis of the probe.

In some embodiments, the probe may incorporate active elements including, but not limited to, organic light emitting diodes and light sensing elements. By collecting diffuse reflectance, fluorescence, and/or Raman scattering spectra, the probe could monitor the hemodynamics and membrane ion channel activity associated with neuronal signaling, and explore tissue composition in the microenvironment near the probe tip. The zero-force connector may be compatible with on-board multiplexing circuitry, which may be necessary with increased functionality of the probe.

The probe design may be optimized for spatial localization in sensing volumes at the tip and distributed along the shank of the probe. For example, the probe may be optimized for the localization of spiking neurons within a few 10 s of micrometers. In some embodiments, recording sites will be ~5 µm or less in diameter to enable cell localization even for synchronous spikes. A zero-force connector may be capable of interfacing ~50 channel probes with commercial electronics.

In some embodiments, the probes may be utilized to form linear arrays that enable the direct perturbation of a neural population code, map long-range interactions causally rather than through correlations, and allow dense optogenetic interrogation of a volume cortical tissue. Combined with the 3-D mapping of neuronal dipoles within this volume, these probes will provide unprecedented investigative capabilities to neuroscientists.

FIG. 1 shows an illustrative embodiment of an exemplary neural probe with high-precision thin film tetrodes arranged in tiers on a cylindrical substrate. The non-limiting exemplary embodiment illustrates a tetrode with first tier 10, second tier 20, and third tier 30; however, it will recognized that other embodiments may include any suitable number of channels. In tetrode embodiments, each of the three tiers includes a set of four conductor lines and electrode sites arranged around the circumference of the cylindrical substrate. All of the electrode sites corresponding to one tier are preferably arranged at approximately the same distance from the tip of the probe. For example, the two visible square-shaped electrode sites of the first tier 10 are about the same distance from the tip of the probe (similarly, two other electrode sites of the first tier 10 that are not visible are at approximately the same distance from the tip). Electrode sites for each the three tiers may vary in distance from the tip of the probe, or in other words, all of the electrode sites of each tier may be offset with respect to the electrode sites of another tier. In some embodiments, the cylindrical substrate may be an optical fiber, which provides an essentially lossless optical channel. The use of thin film conductor lines and electrodes ensures that the diameter of the finished probe is only very slightly larger than the fiber (e.g. a few hundred nm).

From preliminary studies, it is known that a 60 µm fiber has the stiffness required for stereotaxical targeting to depths of at least 1 cm, and probably much more. In some embodiments, the diameter of the neural probes discussed herein are equal to or less than about 60 µm. In other embodiments, the diameter of neural probes is equal to or less than about 30 µm. In some embodiments, electrode design may include at least 6 tiers of 4-channel sensors (tetrodes). These electrodes may be on 10 µm pitch to acquire the rich data set needed to map the positions of neuronal dipoles with a precision equal to 5% of the recording volume (50 µm linear accuracy). It is anticipated that the shaft of the fiber may block the view of electrodes on the side of the probe in some cases, as such the discussion of fabrication technology below assumes 8-channel sensors. Site diameters may be equal to about 5 µm or less, which should enable mapping of synchronous spike activity.

While elegant work has been carried out in fitting probes with optical fibers, waveguides, and organic light emitting diodes, none of these technologies is fundamentally capable of high precision 3-D mapping of simultaneous neural activity in deep brain structures like the neural probes discussed herein.

In some embodiment of an optrode, light is emitted only from the optical fiber tip, which allows stimulation of only one part of a neural circuit at a time. However, most cortical circuits extend in a column along a direction perpendicular to the cortical surface. The function of these circuits can only be understood by investigating the causal interactions of its parts, which requires the ability to deliver light at several points along the shaft in addition to the tip.

Other researchers have mounted micro-inorganic light emitting diodes (µ-ILEDs) at intervals along a probe. An optical fiber provides a conical illumination pattern, whereas a µ-ILED provides an omnidirectional pattern. However, it is unlikely that µ-ILEDs could be transfer-printed on fine substrates (e.g. 30-60 µm) discussed for the present invention. The smallest substrates shown were much larger (~400 µm across). For example, the LEDs themselves are about the same size as the diameter of a 60 µm fiber and could not conform to the cylindrical fiber shape. Moreover, optically-gated in-vivo electrophysical data was taken using wire electrodes epoxied to a "rigid" µ-ILED device, which may indicate fundamental difficulties with the approach. A high processing temperature (~800° C.) makes direct growth of inorganic LEDs using ion beam assisted deposition, for example, highly problematic.

In some embodiments, it may desirable to integrate thin film devices on a fiber substrate. In some embodiments, the optrode may utilize one or more LEDs, photodiodes, or the like at intervals along the probe. The use of such integrated light sources may decouples the light delivery requirement from the choice of substrate and eliminates the need for a laser. In some embodiments, the probes discussed herein may use the Kodak small molecule LED (SMOLED) process, described in detail in Govindarajan, V S, "*Fabrication of Organic Light Emitting Diodes by Flash Vaporization*," 2010 MS Thesis, University of Cincinnati, which is fully incorporated herein by reference. This flash vaporization process may be utilized to fabricate an integrated optrode with µ-SMOLED light sources at intervals along the probe. Thin film organic LEDs, however, could be integrated with a wiring network using the optrode manufacturing process discussed herein. For example, all the layers of the Kodak manufacturing process for fabricating small molecule LEDs (SMOLEDs) are formed by flash evaporation, a process which could be easily integrated with the method of forming the integrated wiring network discussed herein. Similarly, thin film photodiodes for monitoring light intensity and measuring fluorescence of biomolecules or thin film transistors for multiplexing on-probe functions could be integrated with probe wiring.

Figure 2:
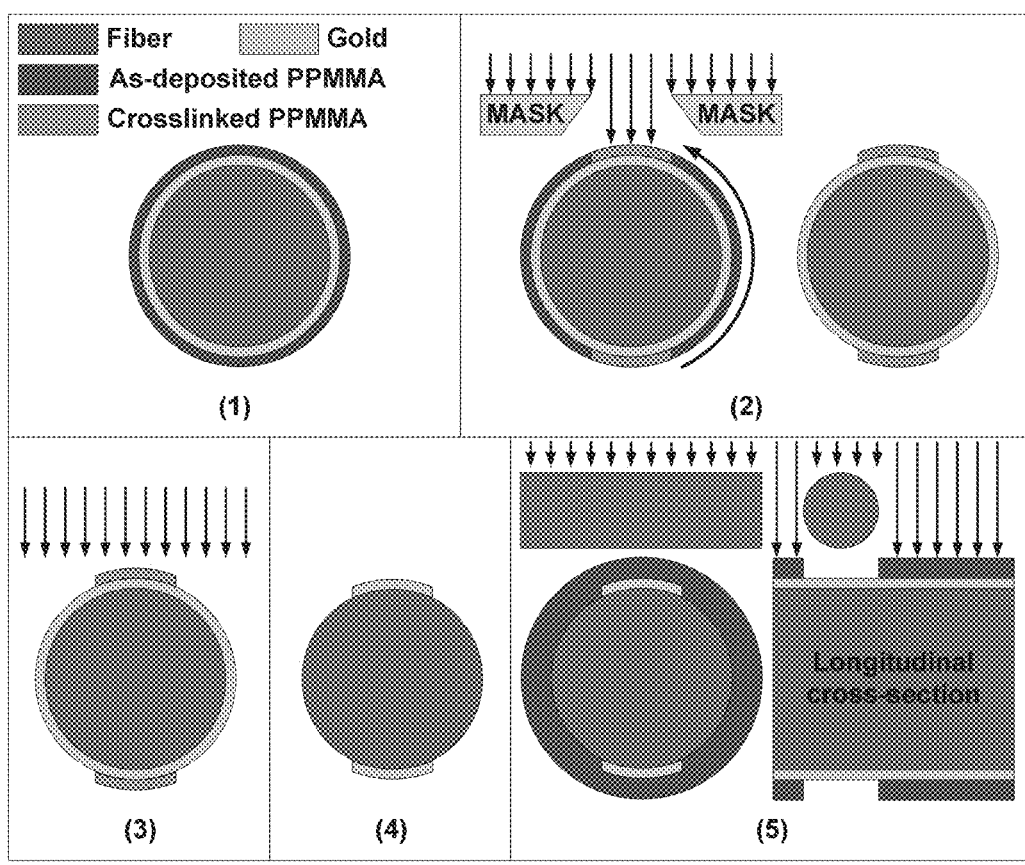
FIG. 2 is an illustrative embodiment of process flow diagram for 2-channel probe prototypes.

FIG. 2 shows an illustrative fabrication process. In step 1, the fiber is coated with sputtered gold and plasma polymerized methyl methacrylate (PPMMA), the plasma-deposited resist that becomes insoluble in a developer (amyl acetate) when it is irradiated by high energy ions. In step 2, resist lines are sequentially exposed on opposite sides of the fiber using a mask illuminated by a broad beam of 30 keV He ions or atoms. While this example discussed two exposures on opposite sides, in other embodiments that desire more than two conductor lines, additional exposures may be necessary. Resist lines remain after development (right, step 2) that protect the conductor lines during sputter etching (step 3), which removes the unprotected gold to form gold conductor lines and electrode sites. The formed gold conductor lines and electrode sites are exposed after removal of the remaining resist in an $O_2$ plasma (step 4). In step 5, the probe is again coated with resist and exposed using a wire perpendicular to the fiber to protect the electrode sites from ion exposure. The resist over the electrode sites clears on development to expose the electrode sites, while the exposed resist remains as an insulating layer and protective overcoat on other portions of the gold.

Figure 3:
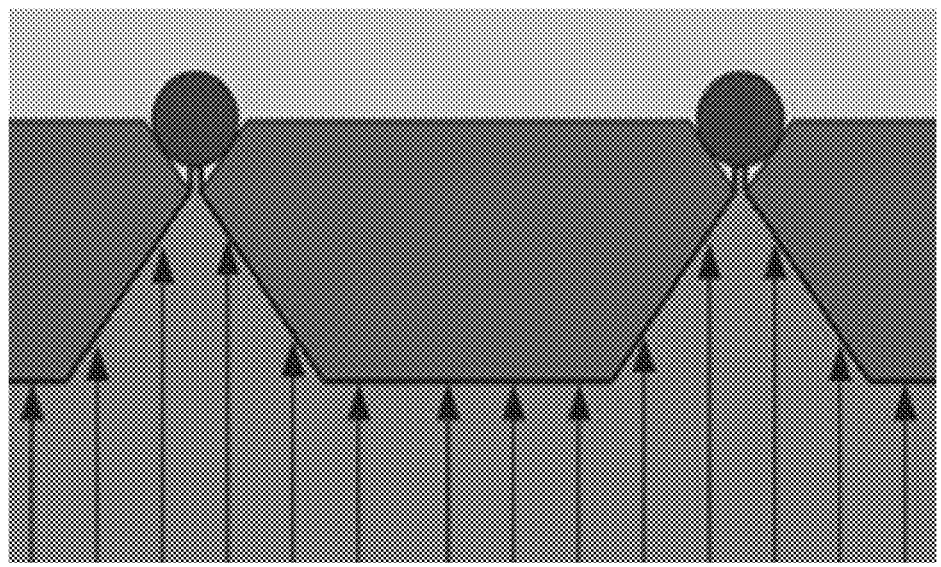
FIG. 3 is an illustrative embodiment of exposure of resist lines on a fiber using a micromachined silicon jig.
Figure 4:
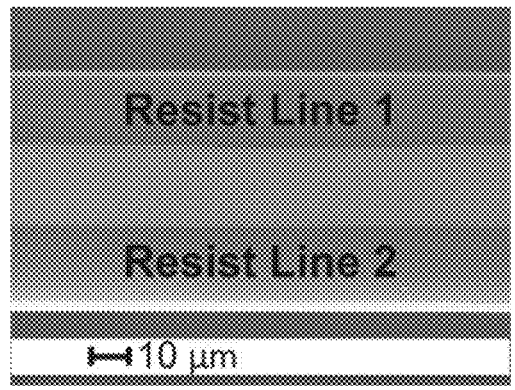
FIG. 4 is an illustrative embodiment of two perfect 25 µm wide resist lines on a fiber 5 cm in length.
Figure 5:
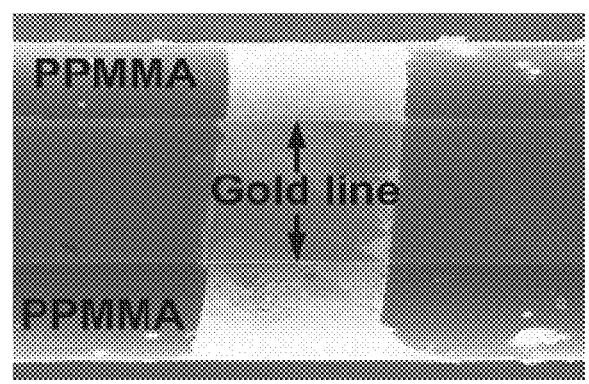
FIG. 5 is an illustrative embodiment of 15×15 µm² electrode site over a gold line.

Critical aspects of the process for alignment of the conductor lines and electrode sites are in step 2 where the mask must be aligned to the fiber over its entire 3 cm length, and in controlling rotation during the multiple exposures of step 2, the sputter etching of step 3, and the formation of the electrode sites in step 5. Mask-to-fiber alignment is accomplished by an exemplary micromachined silicon jig shown in FIG. 3. The jig is formed by two families of intersecting V-grooves anisotropically etched into opposite sides of a (100) silicon wafer. The depth of the upper grooves is chosen so that the fiber extends a small distance above the plane of the wafer. The depth of the lower grooves determines the width of the rectangular opening between the top and bottom grooves. Very light springs force the resist-coated fibers to the bottom of the grooves, resulting in the exposure of a perfectly aligned resist line when the ion beam (arrows) impinges on the bottom of the jig. This approach is the basis for the alignment strategy that is used to fabricate much more complex tiered-tetrode probes discussed herein. FIG. 4 shows two 25 µm wide resist lines on a 60 µm optical fiber 3 cm in length. The perfect edges are noteworthy. FIG. 5 shows an electrode site on one of the gold lines. The gold conductor line is covered by the exposed PPMMA overcoat (semitransparent in the micrograph) except in the area protected by the wire in step 5 of the fabrication process.

It is also important to provide two openings in the overcoat at the distal end of the probe to allow lead wires to be attached, such as with conducting epoxy. The lead wires may allow the probe to be coupled to an external device, such as data storage, neuroamplifiers, signal processing, or the like. These openings, or vias, which are also formed using transverse wire masks are offset by about 1 mm along the shank to keep them from being short-circuited by the bonding epoxy.

The use of wire masks to form the vias has 2 significant limitations: First, these mask results in wide openings in the overcoat covering because about ¼-⅓ of the fiber's circumference is protected from exposure by the wire mask. The application of a lead wire with conducting epoxy on the external end of the probe would cause electrical shorting of lead wires oriented within 90° from each other. Thus, the technology is likely unsuitable for fabricating 4-channel probes, much less multi-tiered probes, because multiple channel probes will likely have multiple contact lines within ¼ to ⅓ of the fiber circumference. The second limitation is that the wires must be manually aligned with the conducting traces formed in the first step of the process. This will become increasingly difficult and expensive as the traces become finer, and their pitch smaller. A solution for producing multi-channel and/or multi-tier probes is outlined below.

Figure 6:
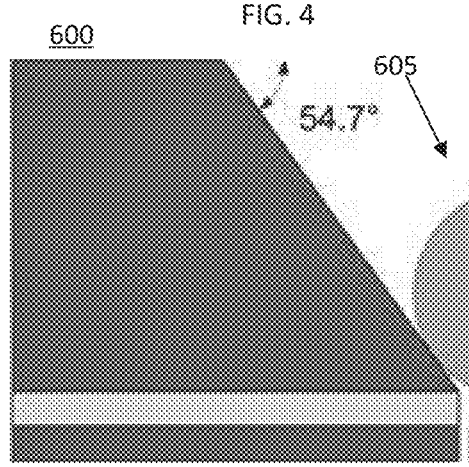
FIG. 6 is an illustrative embodiment of adaptation of V-groove alignment to the fabrication of tiered-tetrode probes.
Figure 6:
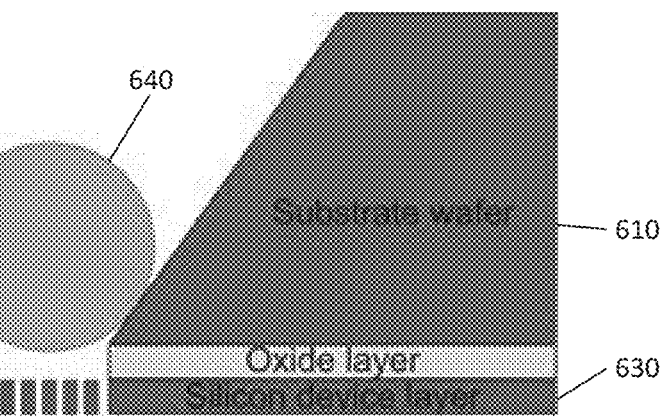

Fabrication process for a single, multi-tiered, and/or multi-channel probe: The process for fabricating single, multi-tiered, and/or multi-channel probes is designed to capitalize on the strengths of the fabrication process discussed above. An alignment jig 600 is shown in FIG. 6, where V-grooves 605 are etched into the substrate wafer 610, such as a silicon-on-insulation (SOI) substrate, and openings 620 for printing the electrodes, conductor lines, and vias are etched into the thinner device layer 630 on the opposite side. While a single V-groove 605 and one cylindrical substrate 640 are shown, it will be understood that multiple v-grooves may be provided by alignment jig 600 to provide simultaneous processing of multiple cylindrical fibers 640. In some embodiments, the silicon wafer 610 may be a substrate that includes one or more layers of materials, such as an oxide layer and silicon device layer 630. Openings 620 form a pattern that is utilized to pattern electrodes, conductor lines, and/or vias on the probe or cylindrical fiber 640. The cylindrical fiber or optical fiber 640 placed in the V-grooves 605 may include at least one electrode layer and at least one resist layer prior to the exposure process. However, in other embodiments, additional layers may be present, such as cladding, additional electrode, and/or insulating or resist layers. The electrode layer may be formed of a conductive or semiconductive material. In some embodiments, the electrode layer may be overcoated with a dielectric material. The resist layer may be formed of any suitable resist material. In some embodiments, the resist layer may be an insulator material.

Figures 7A, 7B, 7C:
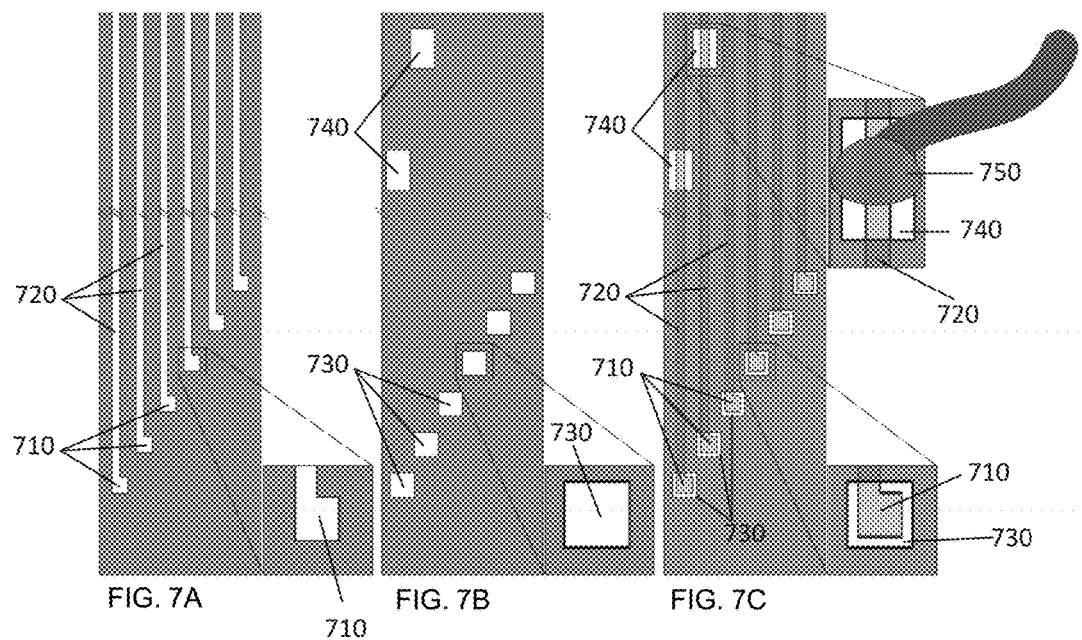
FIGS. 7A-7C are illustrative embodiments of mask A, mask B, and assembly drawing respectively.

Two masks (e.g. Mask A&B) are required to create a multi-tiered neural probe. Illustrative embodiments of two masks are shown in FIGS. 7A-7C. While the masks shown in FIGS. 7A-7C provide six tiers, other embodiments may provide any number of tiers. For example, embodiments for a single tier probe may provide only one pattern for a single conductor line and electrode site; embodiments for a two-tier probe may provide two patterns for two conductor lines and electrode sites; embodiments for a three-tier probe may provide three patterns for three conductor lines and electrode sites; and embodiments for a n-tier probe may provide n patterns for n conductor lines and electrode sites. FIG. 7A shows Mask A, which is utilized to pattern electrode sites 710 and conductor lines 720 on an optical fiber. Optical fibers, which provides at least one electrode layer and at least one resist layer, are place in an alignment jig providing mask A. In some embodiments, Mask A uses a negative tone resist to define the electrode sites and conductor lines. In other embodiments, mask A may be modified for use with a positive tone resist. As discussed previously above with respect to steps 2-4 shown in FIG. 2, the conductor lines and electrode sites may be created in a similar manner utilizing an alignment jig providing mask A. First, the optical fiber may be exposed to ion or atom beams to define resist lines that remain after development. These resist lines define shape of conductor lines and electrode sites to be formed on the optical fiber. This exposure process to define the resist lines may be repeated multiple times after rotating the optical fiber a predetermined amount. The number of exposures performed will determine the number of channels provided by the probe. For example, as a nonlimiting example, each exposure could produce 6 electrodes arranged in tiers on one side of the shank of the probe. The exposure process may be performed four times with the probe being rotated approximately 90 degrees after each exposure to create a tetrode or probe with 4-channels. The four exposures would produce a 6-tier tetrode. After development, only the resist lines remain, whereas other unexposed portions of the resist layer have been removed to uncover the electrode layer. The optical fiber may then be subjected to etching (e.g. sputter etching) to remove uncovered portions of the electrode layer, whereas the remaining exposed resist lines protect electrode materials under these resist lines from the etching, thereby patterning the electrode layer into the contact lines and electrode sites. Next, the remaining resist lines may be removed to uncover the patterned contact lines and electrode sites.

Next, the optical fiber may be overcoated with a nonconductive material or insulator layer. The nonconductive or insulator layer may also act as a resist. FIG. 7B shows Mask B, which is utilized to pattern openings in the nonconductive material layer over openings or vias 730, 740 over electrode sites and a small region of conductor lines. It should be noted that openings and vias are used interchangeably in this disclosure and refer to an exposed portion of a conductor. The optical fiber 640 may be placed in an alignment jig that provides mask B. The openings 730, 740 should be properly aligned with conductor lines 720 and electrode sites 710 before exposure. It should be noted that the openings 730 are offset at different lengths from the bottom of mask B match up with the tiered electrode sites 710. Similarly, openings 740 are offset at different lengths from the bottom of mask B. In some embodiments, Mask B opens a second, positive tone resist coating, over the openings 730, 740. In other embodiments, mask B may be modified for use with a negative tone resist. Note that a fiber stop may be incorporated in each V-groove of the alignment jigs for mask A and B to ensure proper alignment, such as alignment of openings 730, 740 to be patterned with the electrode sites 710 and conductor lines.

FIG. 7C shows the conductor lines and electrode sites with exposed portions after the processing is finished. As discussed above, the vias 740 are offset along the shank so that conductor bands 750 (e.g. conducting epoxy) that connect the lead wires 760 to the thin film conductor lines are not electrically connected by the conductor bands. It will be apparent to one of ordinary skill in the art that mask B allows only one conductor line to be exposed in a plane perpendicular to the conductor line. The exposed areas of the conductor lines are all offset from each other so that no two exposed areas are present in the same plane perpendicular to the conductor lines. Thus, depositing a conductor band over an exposed area of one conductor line in a plane perpendicular to the conductor line will not short with any of the other conductor lines because the other conductor lines will be covered by the nonconductive material layer. While conductor band 750 is shown as a small region covering conductor line 720, the conductor band may form a band around a portion or the entire circumference of the optical fiber. For example, in a probe with six tiers of tetrodes, 24 conductor bands may be positioned on the probe with each conductor band positioned at a different height relative to the tip of the probe. In some embodiments, it may be desirable to repeat the process discussed above to deposit additional electrode layers and insulating layers to form multiple layers on the cylindrical substrate.

In an exemplary example, a manufacturing process may comprise placing cylindrical substrate in a groove provided by a first alignment jig. The cylindrical substrate may be an optical fiber coated with a conductive layer and resist layer. The alignment jig may provide an opening that allows the cylindrical substrate to be exposed. A first mask may be present in the opening of the first alignment jig to define one or more conductor line and electrode sites (depending on the number of tiers desired) on the cylindrical substrate during the exposure. The cylindrical substrate may be optionally rotated a desired amount and subjected to further exposure to pattern additional conductor lines and electrode sites. For example, in the case that a tetrode or 4-channel probe is desired, the cylindrical substrate may be rotated 90 degrees and subjected to exposure three additional times to pattern four sets conductor lines and electrode sites. The resist layer may be removed from the cylindrical substrate leaving a portion of the resist layer remaining in the pattern of desired conductor lines and electrode sites. This remaining resist protects the conductive layer under the remaining resist layer so that removal of the conductive layer (e.g. by sputter etching or the like) leaves the desired conductor lines and electrode sites in a pattern corresponding to the first mask. The remaining resist may then be removed (e.g. using $O_2$ plasma or any other suitable process) to uncover the patterned conductor lines and electrode sites. The cylindrical substrate may again be coated with second resist layer that comprises an insulator material. A second alignment jig providing a second mask may be used to pattern openings or vias in the second resist layer. In other embodiments, the same alignment jig may be utilized, but the second mask may be swapped out with first mask. Portions of the resist may then be removed by any suitable process to form the openings or vias in the second resist layer that expose portions of the patterned conductor lines and electrode sites. The exposed portion of the electrode sites are utilized to monitor electrical responses in a brain, whereas the exposed portions of the conductor lines may be connected to lead wires leading to signal processors, data storage, amplifiers, or the like.

In some embodiments, the manufacturing process steps discussed above may be repeated to create multiple layers of electrode layers and insulating layers on a probe. For example, additional sets of conductor lines and electrode sites may be formed by depositing additionally conductive layers/insulating layers on the cylindrical substrate and repeating the processes with mask A and B discussed above.

Figures 8A, 8B:
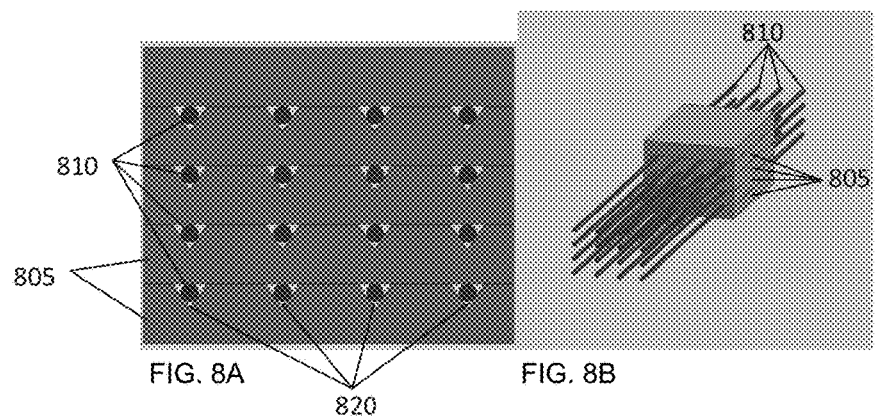
FIGS. 8A-8B are an illustrative embodiment of endview and perspective view of probe array respectively.

Fabrication of probe arrays: We propose to assemble probe arrays using a similar V-groove technology that we used in the alignment jig. An illustrative embodiment of a probe array is shown in FIGS. 8A-8B. A probe array may provide multiple neural probes. A 2-D probe array may arrange the neural probes to gather data in 3 dimensions. While the probe array is 2-dimensional, the array is able to gather 3-D data from the multiple electrode arrays at different depths on each probe. In some embodiments, probe arrays may provide one or more layers with each layer providing an array substrate 805 one or more probes 810. Each array substrate 805 provides one or more v-grooves 820 for receiving probes 810. The probes 810 in each layer of the probe array can be held in place in the v-grooves 820 with glue. FIG. 8A shows an endview of an exemplary embodiment of an assembled probe array on the left, while FIG. 8B shows a perspective view. Probes 810 are multi-tier probes that provide electrode sites at different distances from the tip of the probe. The probe array shown provides 4 layers. These multiple layers of multi-tiered probes allow the probe array to distribute electrodes in a 3-D space and gather 3-D data from the electrode sites.

Experimental Example

The following examples are included to demonstrate particular aspects of the present disclosure. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure.

Understanding the complexity of the brain depends largely on our ability to sense and probe the neural activity. For example, stimulating and recording the neuronal activity from deeper regions in the brain, like the hippocampus is critical to our understanding of the neural circuits. But the researchers are presented with relatively few tools at hand, particularly for in vivo studies. To decode the neural circuitry, selective stimulation of the nervous system at different levels can be now achieved based on recent advances in optogenetics. An optrode, an extensible system architecture is proposed which promises improved reliability, advanced functionality, compatibility with commercial tetrode drives, and parallel-recording infrastructure and software for single unit identification and localization. Optrodes may provide tetrode type electrical contacts integrated on the surface of an optical waveguide. In some embodiments, the optrode features lithographically-defined, thin film conductor traces, dielectric vias, and ultra-low impedance contacts on fine wire, optical fiber, capillary, and/or light-guiding substrates. We have developed two novel fabrication methods, flexible and ultrahigh length-to-diameter ratio (e.g. equal to or greater than 1000) for precise integration of the optical channel and the electrodes.

Neural spikes have been measured in vivo by one channel of a 3 channel probe with $15 \times 15$ $\mu m^2$ recording sites on a 60 $\mu m$ optical fiber in the primary visual cortex of a bush baby (est. layer 5). Spikes were of high SNR (>6.0), allowing clear discrimination of the 3 neurons. Multivariate ANOVA showed strong unit-spike waveform interaction in the 2D space, $F(4, 300)=13.9$, and that the null hypothesis was rejected at $P=1 \times 10^{-10}$. J3, the ratio of the average within-cluster distance to the average between-cluster distance, was 9.6. The optogenetic capacity of the probe in layer 5 of area V1 was tested in another animal. We found neurons that systematically fired spikes in response to each 25 msec laser pulse. At various layers, the spikes recorded from the electrodes of the probes were of sufficiently high quality to accurately map receptive field location, determine stimulus tuning, and even to compute peri-stimulus time histograms (PSTHs) for drifting sinusoidal gratings presented inside the RF. Due to their small diameter these probes displace about 90% less tissue than competing optrodes.

Approach 1—Lithographically Defined Electrode Arrays on Optical Fibers

The first approach is based on an ion or atom beam proximity lithography, a diffraction-free, high throughput imaging technique, that uses energetic helium ions or atoms to carry out lithography on optical fiber substrates. There are two lithography steps. The first defines the conductor lines, and the second creates vias in the insulation where the conductor comes into contact with the cerebrospinal fluid (e.g. FIG. 1). Plasma polymerization of methylmethacrylate (PPMMA) provides a uniform coating of negative tone resist on the needle.

A disruptive core technology enables the integration of sub-micrometer thin film electrodes and associated interconnect wiring on the cylindrical surface of fine optical fibers with tight manufacturing tolerances. The use of optical fibers as probe substrates provides high intensity, multi-spectral light delivery with essentially no coupling loss, as well as the strength and stiffness required for deep-brain applications. The use of thin film conductors contributes negligibly to the probe diameter, high resolution permits a very high electrode count on extremely thin fibers, and high dimensional precision enables accurate 3-D localization of neuronal sources. Moreover, the technology is compatible with high throughput manufacturing at very low cost, an important consideration for wide dissemination of the technology.

Process Flow: (1) Optical fiber substrate—65 $\mu m$ diameter 50 $\mu m$ core, 2.5 $\mu m$ cladding, 5 $\mu m$ polyimide jacket; (2) Au/AuAg alloy deposition via DC magnetron sputtering; (3) Conformal coating of thin resist via PECVD; (4) Ion beam proximity lithography to define conductor lines; (5) Transferring resist pattern into the alloy via sputter etching; (6) Conformal coating of thick resist via PECVD; (7) Pattering of vias for contacts; and (8) Formation of Nanoporous Gold Films (NPG) via wet chemical etching of silver.

Approach 2—Capillary Guided Assembly

Beyond electrophysiology, recent advances in optics, genetics, and biochemistry have enabled the investigation of brain function at various levels via light-based approaches, from intracellular signals to single synapses, cellular response, neural circuit and network, and in vivo behavior.

Figures 9A, 9E, 9F:
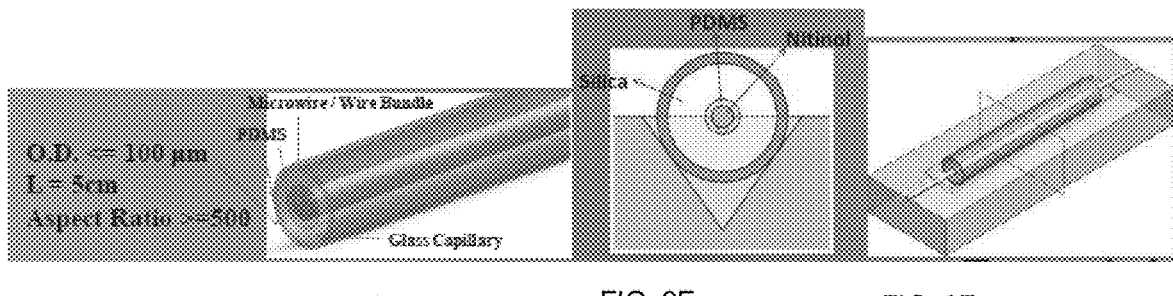

The second approach is based on flexible materials, this device can provide crack-free operation during insertion and longitudinal studies. The fact that the material is "soft" might have important consequence for long-term monitoring. We have developed a precision V-groove guided capillary assembly process (FIGS. 9E-9G) to fabricate OD 100 $\mu m$ device (FIG. 9A) with a single 25 $\mu m$ Nitinol wire, OD 150 $\mu m$ devices on a single 50 $\mu m$ Nitinol wire or on a bundle of three 25 $\mu m$ Nitinol wires (FIG. 9H) over the entire optrode length (ca., 5 cm). We can also assemble OD 100 $\mu m$ device with NiChrome tetrode core. We have calculated the cross-sectional light intensity distribution and the overall intensity versus the propagation distance inside the optrode (FIGS. 9B-9D). An OD 100 $\mu m$ device with a 25 $\mu m$ Nitinol wire has been fabricated and the total transmission is 20.6% measuring in 633 nm wavelength laser. The results suggest highly efficient light transmission from various designs. We also showed preliminary characterization results from our first batch prototype optrodes (FIGS. 9I-9J).

3. Research Strategy

Recent experimental studies using polytrodes and stepped tetrodes have demonstrated very high precision 3-D localization of neuronal current sources by taking advantage of the rich datasets provided by high density, spatially overlapping, electrophysiological measurements. In the stepped probe experiments non-planar tetrodes, which have full spherical sensitivity, were advanced in 5-10 $\mu m$ increments through the visual cortex of macaque monkeys and a cat. A meticulous analysis of errors resulting from uncertainty in electrode geometry, Johnson noise, and model dependent inversion, concluded that an optimal model dipole can account for 96% of the power in the spatial variation of the action-potential amplitude and that neuronal dipoles can be localized within a sphere of ~50 $\mu m$ radius—about 5% of the recording volume of a static tetrode. Although polytrodes have a much smaller recording volume than the stepped tetrode, they can simultaneously record high density, spatially overlapping action-potential samples, a significant advantage that reduces data collection time and the complexity (hence errors) of data analysis. Another polytrode limitation is the inability to target deep brain structures.

In some embodiment, the neural probes discussed herein are a slender (e.g. 30-50 $\mu m$ in diameter) static cylindrical probe with a) efficient light delivery to the tip for optogenetic interrogation of neural circuits, b) the ability to simultaneously record and map all active neurons within the recording volume with very high accuracy, and c) the capability of targeting deep brain regions (e.g. cortical sulci, subcortical structures, and the brain stem), for which micromachined silicon probes are too short.

Approach: Substrates: Multi-mode optical fibers (Polymicro Technologies FVP050055065) with 50 $\mu m$ core, 2.5 $\mu m$ cladding layer, and 5 $\mu m$ polyimide jacket were chosen as probe substrates. Although larger than desired, they were the smallest fibers available at the time. Single mode fibers have since become available from Schott [Puravis GOF 50] with core+cladding diameters of ~35 μm. The first step in the preparation of fiber substrates is to strip the protective jacket (Piranha etch), which is full of embedded particulates and designed to adhere poorly to the fiber substrate. A ~30° taper is then formed on the probe tip, such as by using known etching technique. A new, 320 nm thick, jacket of plasma polymerized styrene (PPS) was applied and cross-linked by 75 keV $He^+$ implantation using a rotary fixture.

Figure 10:
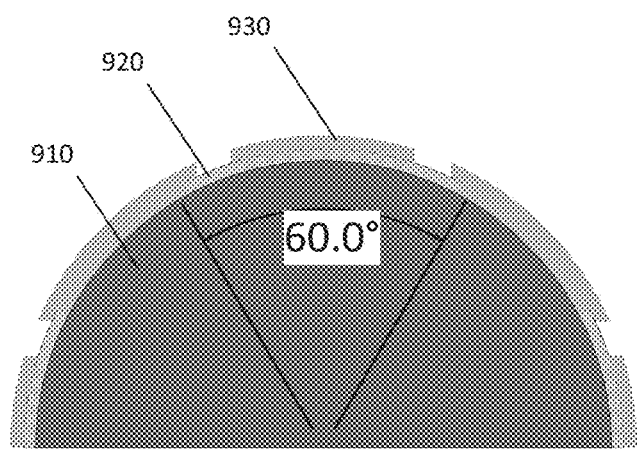
FIG. 10 is a cross-section of a multi-tiered octrode.
Figure 11:
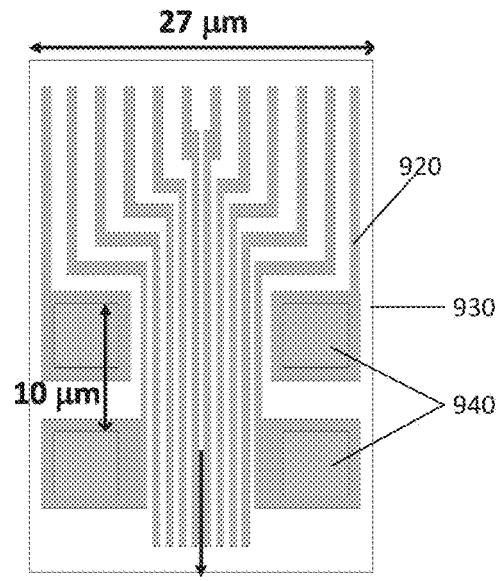
FIG. 11 is a plan view of the circuit panel or wiring layout that subtends a 60° angular field.

Probe fabrication: FIG. 10 is a cross-section of a multi-tiered octrode, or 8-channel sensor, with 5×5 μm² contacts subtending a 60° angle on a 50 μm optical fiber. The circuit has 2-layers on the optical fiber 910: a) a conductor layer 920 containing the electrode sites or pads and the thin-film wiring or conductor lines which connects them to an electronics interface; and b) an insulating layer 930 with openings or vias where the electrode sites or pads make electrical contact to cerebro-spinal fluid. FIG. 11 is a plan view of the circuit panel or wiring layout that subtends the 60° angular field in FIG. 10. The gold conductor layer 920 is covered by the insulator layer 930, except at the electrode sites or contact pads 940. Similarly, openings in the insulator layer 930 that allow the probe to be connected to lead wires (not shown) may be provided on an external end of the optical fiber 910. The first 4 of 12 electrode pads are shown, whereas the arrow points to the remaining 8 pads below closer to the tip of the optical fiber 910. The electrode sites are 7×7 μm² square, while the vias are 5×5 μm² in area. The 1 μm wide border allows for misalignment between the two layers. There isn't much room for the interconnect lines between the pads, which are 0.5 μm wide on 1.0 μm centers. Away from the tip, or upward in FIG. 11, there is more space and the interconnect lines widen to 0.75 μm on 2.5 μm centers. The first step in fabricating both the conductor and insulating layers is lithography. Ion beam proximity printing was utilized, where a broad beam of ~50-75 keV $He^+$ ions illuminates a stencil mask and transmitted beamlets transfer the mask pattern to resist on a substrate. The resist is plasma polymerized styrene (PPS), a negative tone ion resist that uses amyl acetate as developer and with near perfect conformality and the ability to planarize nanoscale voids.

Figure 12:
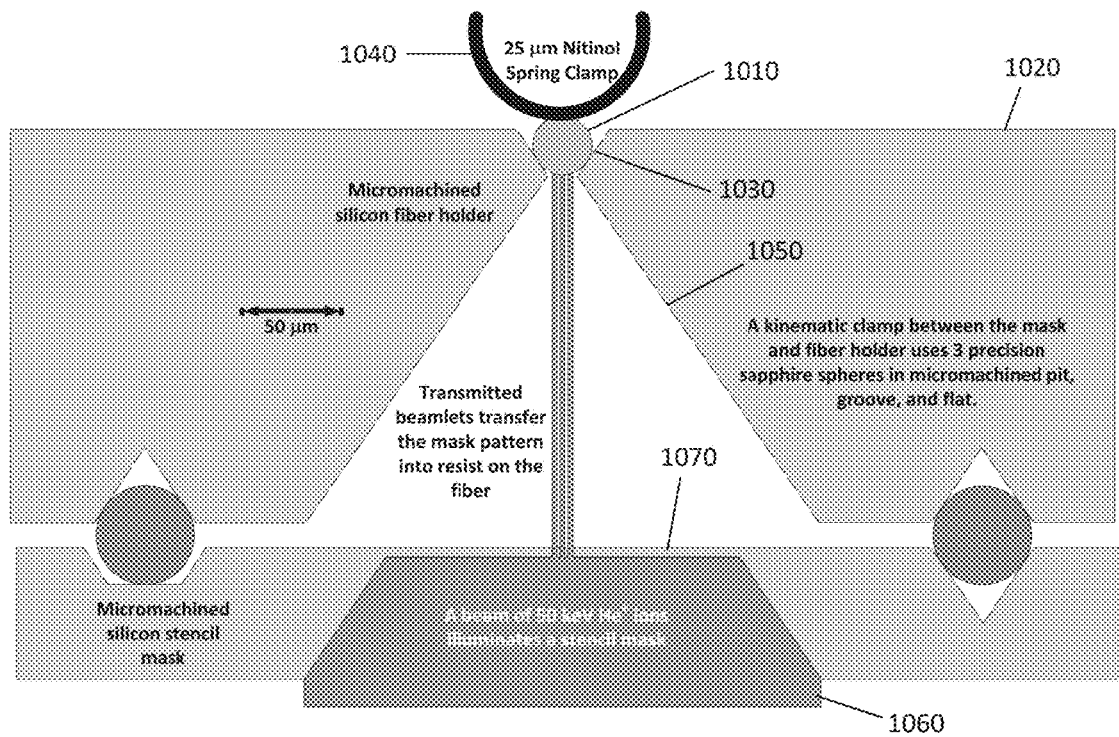
FIG. 12 shows an illustrative example of a jig that may be utilized to print patterns on an optical fiber.
Figure 13A:
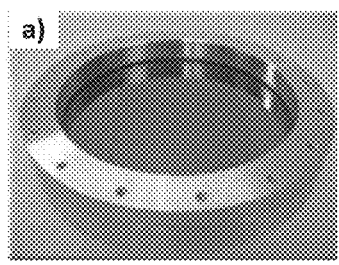
FIGS. 13A-13C show illustrative examples of an alignment, spring clamp holding a substrate in place, and conductor line printed using a V-groove mask.
Figure 13B:
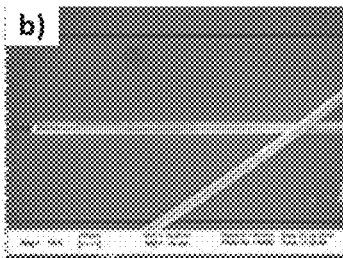
Figure 13C:
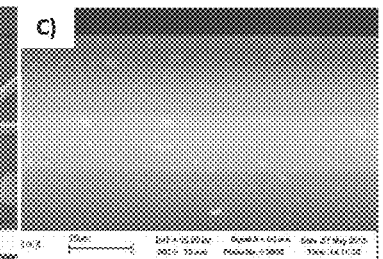

FIG. 12 shows an illustrative example of a jig that may be utilized to print fine, multilayer patterns on an optical fiber 1010. The design builds on V-groove technology that accurately positions optical fibers in 1- and 2D-arrays. The micromachined jig or fiber holder 1020 is formed by two families of intersecting V-grooves anisotropically etched into opposite sides of a (100) silicon wafer. The depth of the upper grooves 1030 is chosen so that the fiber 1010 extends a small distance above the plane of the wafer where it can be clamped with light nitinol springs 1040, such as a 25 μm nitinol spring. The lower groove 1050 is designed to expose, as in FIG. 10, a 60° field on the surface of the fiber. The diffraction limit is ~100 nm. A beam 1060 of ~50-75 keV $He^+$ ions or neutral atoms illuminate a stencil mask 1070, which may be a micromachined silicon stencil mask patterned into the desired conductor lines and electrode sites or the desired openings to be patterned through the insulator layer. Using neutral atoms has advantages particularly for wide spacings between the mask and substrate, because, being neutral, they are intrinsically immune to artifacts caused by the interaction of ions with ambient electromagnetic fields and charge build-up on the mask and substrate. A kinematic clamp between the mask and fiber holder 1020 may utilize 3 precision sapphire spheres in pit, groove, and flat mounts. High throughput can be achieved by printing many fibers at the same time. For example, some jigs may provide multiple grooves that allow several optical fibers to be processed. A 50-groove fiber holder on a 10 cm silicon wafer is shown in FIG. 13A. FIG. 13B shows a 50 μm nitinol wire held in one of the grooves by a 50 μm nitinol spring clamp. The intimate contact between fiber and groove ensures accurate center-to-center alignment of the fiber with the groove. The wire is so straight that only one spring is required per inch of length. Clamping of optical fibers is similar. The ion beam lithography tool can expose PPS resist over the entire field in 12 seconds, corresponding to a throughput of about one 4-sided probe/second (without overhead). FIG. 13C shows one of four 15 μm wide gold lines on a 65 μm wide fiber that was printed using an early V-groove mask.

The stencil masks are ~3 μm thick silicon membranes with dry etched transmission windows. The stencil masks contain a high precision pit, groove, and flat pattern of a kinematic mount that registers to 3 sapphire balls secured in pits to the fiber holder. Successive mask levels are thus automatically registered to each other. Layer-to-layer registration accuracy is expected to be about ±0.5 μm (3σ), adequate for centering the via in the insulating layer on the electrode pad. Four prints, each with a 90° fiber rotation, are required to pattern the entire probe surface. Angular alignment and longitudinal registration is referenced in each exposure to a 4 mm cubic bead that is glued to each fiber before processing begins. This bead serves as a handle during process and as a stop for locating the fiber in the V-groove zero-insertion-force connector discussed below. Commercial Swarovski beads, which were used to fabricate probes for collecting preliminary data, seem to have the required accuracy, but this requires further investigation. A high precision micromachined jig may be used to center the bead at a specified distance from the probe tip. The resolution limit of the printing process, mainly due to diffraction, is about 0.1 μm making the 0.5 μm line-space pattern of the interconnects between the electrode pads well within the capability of the technology.

This experimental setup allowed 6 probes to be processed at the same time. The conductor layer is deposited by DC-magnetron sputtering and etched in an ion mill. The tool set that developed specifically for patterning non-planar substrates includes an ion printer, DC-sputtering tool, PECVD resist coater, and an ion mill.

Figure 14A:
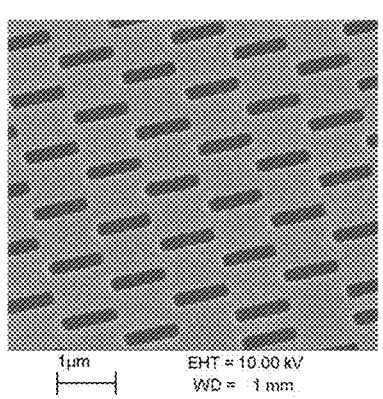
FIGS. 14A-14B show a section of the mask used for printing 0.25 µm interdigitated electrodes and a surface acoustic wave mask.
Figure 14B:
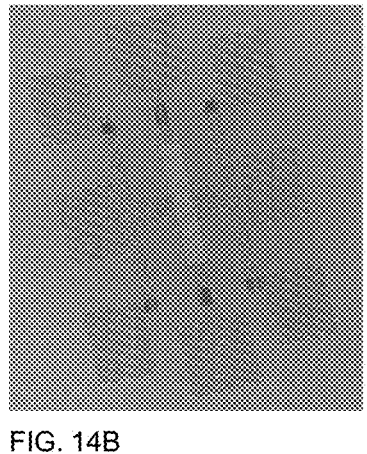

Mask technology: Masks are crucial to any successful probe manufacturing process. In Stumbo et al., "Fabrication of 0.25 μm surface acoustic wave devices by ion beam proximity printing." J. Vac. Sci. Technol. B. Vol. 9, pp. 2879-2881, new ground broke in terms of the resolution and complexity of circuits that could be fabricated. FIGS. 14A-14B show a section of the mask used for printing 0.25 μm interdigitated electrodes and surface acoustic wave mask. It is made up of parallel rows of rectangular 1.0×0.25 μm² transmission windows on 1.0 μm pitch. The mask was printed twice with a 1.0 μm offset along the rows to create continuous 0.25 μm lines about 15 μm in length. A mask with freestanding 15×0.25 μm² bars would be incredibly floppy; the double exposure strategy solves this problem. More recent studies conclude that stitching errors can be controlled even to the exacting standards of IC manufacturing. We shift the pattern on the substrate between exposures by tilting a clamped mask/substrate assembly relative to the beam, currently using a motorized tip/tilt mirror mount which can achieve 10 nm pattern placement accuracy. FIG. 14A shows a section of the mask used for printing 0.25 μm interdigitated electrodes.

Figure 15:
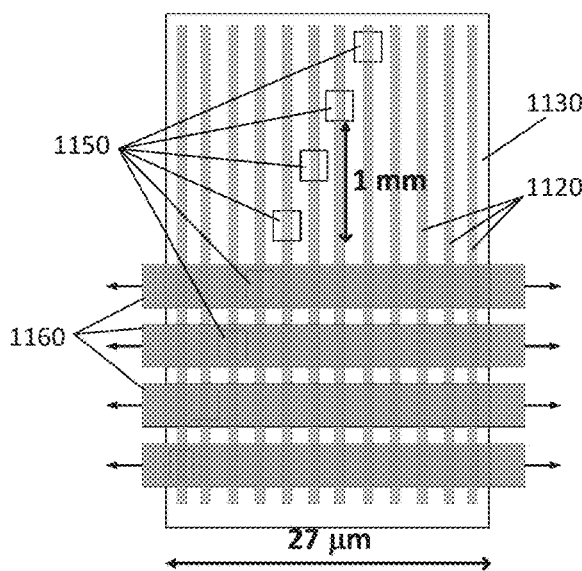
FIG. 15 shows a wiring diagram for a section of an interface region on the external end of the probe.
Figure 16:
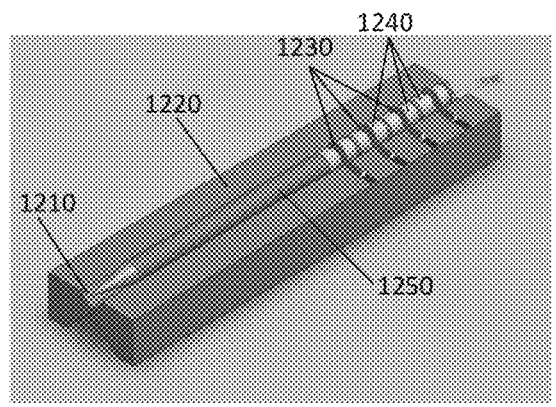
FIG. 16 is an illustrative example of a connector for a neural probe.

Interface connector: An important part of probe technology is the development of a zero-insertion-force (ZIF) connector to interface the probe with signal processing electronics. FIG. 15 shows the wiring diagram for a section of the interface region on the external end of the probe. The upper half of the figure shows vias 1150 over the conductor lines 1120 that are 250 µm long on 500 µm pitch in the direction parallel to the probe and 3.0 µm wide in the transverse direction. Conductor lines 1120 is covered by insulating layer 1130, except at vias 1150. The lower half of the figure shows 300 µm wide conductor bands 1160 (e.g. aluminum bands) that completely encircle the probe. Each conductor band 1160 makes electrical contact with a single conductor line 1120 through a corresponding via 1150. The ZIF connector (FIG. 16) comprises an oxidized V-groove 1210 on a silicon substrate 1220 and a linear array of gold-coated nitinol springs 1230 for securing the probes 1250, where each spring contacts one of the aluminum bands 1240. A cam device (not shown) lifts all of the springs at the same time when the probe 1250 is inserted or removed, thus making it a zero-force-insertion device. The springs 1230 are bonded to a wiring pattern on the wafer that could incorporate multiplexing electronics. The cubic bead that was attached to the fiber at the beginning of processes serves as a stop to ensure proper registration between the springs and the aluminum bands. The concept is easily extended to linear arrays.

Preliminary data: Optogenetic targeting and electrical recording. Probes were fabricated as described above except that the lithography jig was the rather crude prototype. Four adult male prosimian primates (*Otolemur garnettii*) weighing 0.9-1.1 kg were used in these experiments according to protocols approved by the IACUC at Vanderbilt University. The animals were anesthetized, paralyzed, and artificially respirated. A craniotomy and durotomy were made over the lateral geniculate nucleus (LGN) and the lateral pulvinar (PL) nucleus of the thalamus at Horseley-Clarke coordinates A-P 3 and M-L 7. An injectrode filled with a concentrated preparation ($10^9$ iu/ml) of the VSVg-pseudotyped lentivirus carrying the CHR2-GFP gene behind the α-CAMKII promotor (Addgene plasmid 15814, FCK-CHR2-GFP; UNC Vector core, NC) was then inserted into the region of PL containing neurons with central receptive fields and 0.8 µL of the virus was injected over 30 minutes. The animal was revived and returned to the cage. Minimum 6 weeks were allowed for the transfected neurons to express CHR2-GFP. After 6 weeks, one of the animals was perfused and coronal sections of V1 and thalamus were examined for GFP fluorescence. Neurons within 500 µm of the injection in PL were strongly labeled for GFP. Axons expressing GFP were found in layers 1-3 of area V1. Neurons in layer 5 of V1 also strongly expressed GFP, through retrograde transport of the injected virus particles. These findings are consistent with previous anatomical studies that reported area V1 sends projections from layer 5 to PL and receives inputs from PL in layers 1-3. Two other animals were used, more than six weeks after the injection, for testing the probes. Using the same surgical methods, a craniotomy and durotomy were made over area V1. The fiber on the probe was connected to a 100 mW DPSS 473 nm laser source (Shangai Laser and Optics Company Ltd) with ferrules and a ceramic sleeve (Thorlabs, N.J.). The electrodes on the probe were connected to a Blackrock multichannel recording system. The probe was inserted into area V1. We observed no flexing and the probe remained straight and stiff as it passed through the pia mater and advanced through the cortex. FIG. 17 shows a surgical microscope photo of cortical penetration of the probe. The probe is about 1.1 mm inside the cortex. About 1.5 cm thick agarose covers the cortical surface and embeds the probe, to increased stability. The straight advance of the probe is clear by comparison to the reference line. At different layers of V1 (identified by their depth and characteristic electrophysiological responses), the probe was positioned so as to record extracellular spikes. Neural spikes measured in vivo by one channel of a 3-channel probe at a depth of 1173 µm from the cortical surface are shown (FIG. 18A-18C). FIG. 18A shows spikes collected on 1 channel of a 3-channel probe clearly show 3 distinct neurons. High SNR allowed separation of spike waveforms into 3 units. FIG. 18B shows spike clusters (dots) and the template region (oval) on a 2D feature space. FIG. 18C shows pikes collected under similar conditions using a high-impedance commercial tungsten electrode. Comparison shows probe data have higher amplitude spikes (higher SNR). Spikes were clustered in the principal component space using an adaptive K-means algorithm and the mean template was computed for each distinct cluster. Results showed that the probe sampled activity of three distinct neurons on this channel alone. Spikes were of high SNR (>6.0), allowing clear discrimination of the 3 neurons. Multivariate ANOVA showed strong unit-spike waveform interaction in the 2D space, $F(4, 300)=13.9$, and that the null hypothesis that all spike waveforms came from the same underlying normal distribution in the 2D feature space was rejected at $P<10^{-10}$. J3, the nonparametric measure of sorting quality, which is the ratio of the average within-cluster distance to the average between-cluster distance, was 9.6. For comparison, a high-impedance single tungsten electrode (1.1 MΩ, FHC Inc.) was inserted to about the same depth in the same cortical area and spikes were collected and sorted using the same state-of-the-art equipment and methods. The results showed the spikes collected by our probes were of greater amplitude (600 mV to 130 mV at the same gains and filter bandwidths), higher SNR, and allowed for better discrimination of neurons (FIG. 18A-18C).

To test the optogenetic capacity of the probe, we inserted the probe in area V1 of another animal and advanced the probe till we found layer 5 excitatory cells. Five successive pulses of laser, each 25 msec long, separated by inter-pulse-interval of 25 msec were delivered for a total of 250 msec. Neural responses were band-pass filtered at 250 Hz-7.5 KHz to remove any potential photoelectric effects at 0.7 Hz-170 Hz. No slow fluctuations were observed in the filtered signals at either 4 Hz (1/0.25 sec) or 20 Hz (1/0.05 sec) or their first 5 harmonics. The filtered signals were then thresholded at 3.25×r.m.s value and spikes from a single unit were sorted using the online clustering algorithms in the Cerebus software suite. In layer 5, we found neurons that systematically fired spikes in response to each 25 msec laser pulse. The spikes were time-locked to the laser onset. FIG. 19 shows a histogram of the in-vivo neural response to 5 laser pulses. At various layers, the spikes recorded from the electrodes on the probes were of sufficiently high quality to accurately map receptive field location, determine stimulus tuning, and even to compute peri-stimulus time histograms (PSTHs) for drifting sinusoidal gratings presented inside the RF.

Validation: Optogenetics and our post-mortem histological capabilities allow quantification of the validity of our source localization method. An example illustrating the procedure is shown (FIG. 20A-20B). Coronal section of area V1 is shown FIG. 20A with layers marked. White boxed region of layer V in high magnification fluorescence (FIG. 20B) shows several excitatory pyramidal cells expressing ChR2-GFP. Schematic illustration of our validation method is shown superimposed. Probes will be dye-coated to mark the tip (triangle at the top left corner of FIG. 20B). Laser should activate some of the ChR2-expressing neurons whose spikes will be recorded by the tetrode(s) on the probe and their dipole sources estimated. Coronal sections, 40 µm thick, will be collated and serially reconstructed, and estimated dipole source locations will be marked on them (e.g., asterisks 2010 in FIG. 20B). After testing the probes, the animal was perfused. Coronal sections were cut and reacted in one of the following 3 (rabbit-grown) antibodies: i) 1:50 anti-α-CAMIIK (Santa Cruz) ii) 1:500 anti-GABA (Sigma) iii) 1:1000 anti-GFAP (Upstate/Millipore). All cells expressing GFP co-localized α-CAMIIK but not GABA or GFAP, ensuring that the cells whose spikes were recorded by the probe during laser-activation can be clearly identified in the processed slices (cells C seen in FIG. 20B).

Embodiments described herein are included to demonstrate particular aspects of the present disclosure. It should be appreciated by those of skill in the art that the embodiments described herein merely represent exemplary embodiments of the disclosure. Those of ordinary skill in the art should, in light of the present disclosure, appreciate that many changes can be made in the specific embodiments described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure.

What is claimed is:

1. A neural probe system comprising:
    a cylindrical substrate for a neural probe with multiple tiers and multiple channels;
    an electrode layer disposed on the cylindrical substrate, wherein the electrode layer is patterned into a plurality of contact lines where each channel of the multiple channels comprises a set of multiple contact lines of the plurality of contact lines, each of the plurality of contact lines providing an electrode site, each tier of the multiple tiers are offset at different distances from a tip of the neural probe, and the electrode sites corresponding to each tier of the multiple tiers are arranged at approximately the same distance from the tip of the neural probe; and
    an insulator layer disposed over the electrode layer, wherein openings in the insulator layer are provided at the electrode sites for each of the plurality of contact lines.

2. The neural probe system of claim 1, wherein the electrode layer provides four channels, and each of the four channels comprise six tiers.

3. The neural probe system of claim 1, wherein vias in the insulator layer are provided over a portion of the contact lines, and
    a plurality of conductive bands positioned around the cylindrical substrate, wherein the each of the plurality of conductive bands is aligned over one of the vias in the insulator layer.

4. The neural probe system of claim 3, wherein the neural probe is positioned in a probe array with additional probes, the probe array comprising an array substrate providing an array of grooves, wherein each of the neural probe and the additional probes is positioned into one of the array of grooves of the array substrate.

5. The neural probe system of claim 4, wherein the array substrate provides a plurality of springs for securing the neural probe and each of the additional probes, and each of the plurality of springs contacts one of the plurality of conductive bands or an additional conductive band of the additional probes.

6. The neural probe system of claim 4, wherein additional array substrates providing additional layers of probes are stacked on top of the array substrate to form multiple array levels.

7. The neural probe system of claim 4, wherein each of the additional probes is a multi-channel, multi-tiered probe comprising:
    a core,
    a plurality of additional contact lines and additional electrode sites positioned on the core, wherein the additional contact lines and additional electrode sites are arranged into multiple sets of channels comprising a portion of the additional contact lines and additional electrode sites, each channel of the multiple sets comprises multiple tiers that are offset at different distances from a tip of the core,
    an insulator disposed on top of the plurality of the additional contact lines and additional electrode sites, wherein the insulator provides a plurality of first openings to upper portions of the additional contact lines and a plurality of second openings to the additional electrode sites, and
    a plurality of conductive bands each positioned on the core over one of the plurality of first openings.

8. The neural probe system of claim 7, wherein the multiple sets of channels provides four channels, and each of the four channels comprise six tiers.

9. The neural probe system of claim 7, wherein a diameter of at least one of the additional probes is equal to or less than 60 µm, all of the additional electrode sites for the at least one of the additional probes are positioned within 60 µm from the tip of the core, and the additional electrode sites have diameters equal to or less than 5 µm.

10. The neural probe system of claim 7, wherein the additional probes provides at least one thin film Light Emitting Diode (LED) or photodiode.

11. The neural probe system of claim 7, wherein the additional probes provides a spatial resolution of 75 µm or better.

12. The neural probe system of claim 7, wherein a first array substrate provides a plurality of springs for securing the additional probes in a plurality of v-grooves, and each of the plurality of springs contacts one of the plurality of conductive bands.

13. The neural probe system of claim 1, wherein the neural probe provides at least one thin film Light Emitting Diode (LED) or photodiode.

14. The neural probe system of claim 1, wherein a diameter of the neural probe is equal to or less than 60 µm.

15. The neural probe system of claim 1, wherein all of the electrode sites are positioned within 60 micrometers from a tip of the cylindrical substrate.

16. The neural probe system of claim 1, wherein each of the electrode sites has a diameter equal to or less than 5 µm.

17. The neural probe system of claim 1, wherein the neural probe provides a spatial resolution of 75 µm or better.

18. The neural probe system of claim 1, wherein the neural probe is formed via a method comprising:

positioning the cylindrical substrate in a first jig, wherein the cylindrical substrate is coated by the electrode layer and a resist layer, and the jig comprises at least one v-groove for receiving the cylindrical substrate and a first stencil mask defining a first pattern for a portion of the contact lines and the electrode sites;

exposing said cylindrical substrate to a first broad beam of energetic ions or neutral particles, wherein said first broad beam transfers said first pattern to the resist on the cylindrical substrate;

removing a portion of the resist from the cylindrical substrate, wherein remaining resist corresponding to the first pattern is unremoved from the at least one cylindrical substrate;

removing an exposed portion of the electrode layer from the at least one cylindrical substrate, wherein the remaining resist left on the cylindrical substrate prevents a portion of said electrode layer below the remaining resist from being removed, thereby forming the first pattern for the portion of the contact lines and the electrode sites from the electrode layer; and removing the remaining resist from the cylindrical substrate, wherein removing the remaining resist uncovers the first pattern for the portion of the contact lines and the electrode sites.

* * * * *